(12) United States Patent
Solomon et al.

(10) Patent No.: US 6,551,684 B1
(45) Date of Patent: Apr. 22, 2003

(54) MEMBRANES AND METHODS OF MANUFACTURE THEREOF

(75) Inventors: David Henry Solomon, Officer (AU); Greg GuangHua Qiao, Doncaster East (AU); Marcus Julian Caulfield, Ashburton (AU)

(73) Assignee: Gradipore Limited, Frenchs Forest (AU)

(*) Notice: Subject to any disclaimer, the term of this patent is extended or adjusted under 35 U.S.C. 154(b) by 0 days.

(21) Appl. No.: 09/645,956

(22) Filed: Aug. 25, 2000

(30) Foreign Application Priority Data

Aug. 18, 2000 (AU) .................................................. 9521/00

(51) Int. Cl.7 .............................. B32B 3/06; B32B 9/00
(52) U.S. Cl. ........................ 428/103; 428/105; 428/107; 428/156; 428/175
(58) Field of Search ................................. 428/116, 117, 428/118, 174, 411.1, 103, 105, 107, 175, 156, 195, 196

(56) References Cited

U.S. PATENT DOCUMENTS

| 4,787,982 A | 11/1988 | Caro et al. |
| 5,167,825 A | 12/1992 | Lipski et al. |
| 5,266,207 A | 11/1993 | Boye et al. |

FOREIGN PATENT DOCUMENTS

| DE | 19860265 | * | 6/2000 | ............ H01J/49/04 |
| EP | 0 503 596 B1 | | 6/1996 | |
| EP | 1 013 336 A1 | | 6/2000 | |
| EP | 1013336 | * | 6/2000 | ............ B01D/69/00 |
| SU | 1699561 A1 | | 12/1991 | |

* cited by examiner

*Primary Examiner*—James J. Seidleck
*Assistant Examiner*—Travis B Ribar
(74) *Attorney, Agent, or Firm*—Baker & McKenzie

(57) ABSTRACT

A polymeric membrane system containing a polymeric membrane and a substrate with interstitial gaps. Polymeric membrane components reside within the interstitial gaps of the substrate and below the surface of the substrate. Also, the layer of polymeric membrane components is thinner than the cross-sectional thickness of the substrate.

22 Claims, 7 Drawing Sheets

(a)

(b)

MEMBRANES AND METHODS OF MANUFACTURE THEREOF

FIELD OF INVENTION

The present invention relates to membranes. In particular, the present invention relates to membranes including, but not limited to, thin membranes and to methods of making such membranes.

BACKGROUND

Generally membranes can be defined as selective barriers between two phases. Separation is achieved when some species are transported to a greater extent from one phase to the other. The driving force for the movement of molecules includes concentration differences, electric potential differences (charge) and pressure differences. The rate of transport of molecules through membranes is governed by several factors including pore size, thickness of membrane, membrane fouling rates, etc.

A wide variety of different materials have been utilized for producing membranes. Generally microporous membranes can be divided into two main groups: those formed physically and those formed chemically. Membranes can also be controllable formed by careful manipulation of the solubility of polymers in solution. These physically formed membranes can be produced by either diffusion induced phase separation techniques (DIPS) or temperature induced phase separation (TIPS).

Physically formed membranes are useful for many applications including water purification, dialysis and protein separation. However, the techniques for reliably producing membranes of controlled pore size are often complicated, expensive and not easily reproduced in the laboratory.

Chemically produced membranes are made via a series of chemical reactions to form three-dimensional polymer networks. Thin polymer networks are not generally mechanically strong and are often supported in order to make useful products. The support or substrate is generally made from a material that is relatively inert, has good wet strength and not likely to readily bind proteins. Examples of substrates that have been used previously include fiberglass, polyethyleneterapthalate (PET) and woven nylon.

Recently, a need has arisen for membranes having the following characteristics:
- controlled pore size
- provide rapid separation
- good mechanical strength
- be free of soluble impurities
- defect free
- water resistant Current methods for producing suitable membranes produce relatively thick membranes with a tendency for large numbers of defects. Whilst they tend to have good mechanical strength, their thickness results in some disadvantages. First, they have slower separation times compared to thin membranes. Second, they require more processing (eg more washes) to remove soluble entities from the membrane. In the case of the aqueous system, water soluble entities are removed. It is highly desirable to remove such water soluble entities, for example residual monomer, as they may react with the species being separated, resulting in an impure product and possibly toxic in nature. In the case of the organic systems, organic soluble entities are removed.

Supported membranes have conventionally been formed on a substrate by casting a membrane-forming polymer between two glass plates. A characteristic of membranes formed by this process is that they have a glossy/shiny appearance. This glossy appearance is the result of the membrane having a continuous polymeric layer over the substrate (see FIG. 1($a$)). That is, the resultant membrane is thicker than the substrate.

To produce a thinner membrane according to such conventional methods, a thinner substrate is used. In the case of non-woven substrates, as the substrate becomes thinner, the distance between the fibrils in the substrate increases. At a certain distance, the polymeric layer is no longer able to completely fill in the interstitial spaces between the fibrils of the substrate. This results in the formation of holes in the continuous polymeric layer, producing a defect and a non-functional membrane. In the case of woven substrates, as the substrate becomes thinner, the fibre diameter of the substrate decreases, and with it, a reduction in gel holding ability.

We have discovered that, surprisingly, a functional membrane can be achieved by filling the interstitial gaps or spaces in a substrate with a polymer, preferably crosslinked (see FIG. 1($b$)), without forming a continuous constant thickness polymeric layer over the substrate as in the case of conventional membranes. Such membranes, because of their unique structure, have a matt or non-glossy appearance on at least one side, in contrast to the glossy appearance of membranes produced by the conventional methodology described above.

In a first aspect, the present invention provides a polymeric membrane system comprising a substrate and a polymeric membrane, wherein the substrate comprises a plurality of interstitial gaps therein and wherein the polymeric membrane comprises polymeric membrane components spanning the interstitial gaps of the support, the polymeric membrane components being thinner than the substrate.

Preferably the polymeric membrane system of the invention has no detectable soluble entities. In the case of aqueous systems, water soluble entities are not detectable. In the case of organic systems, organic soluble entities are not detectable. Most preferably, the system has no detectable residual monomer(s).

An advantage of forming the membrane in the interstitial gaps of the substrate is that the thickness of the support is not governed by the thickness of the membrane. Therefore, the thickness of each membrane component spanning the interstitial gaps can be decreased so that they are effectively below the surface of the substrate. Thus, the design of the membrane is such that a thin membrane can be achieved while using a substrate that is of sufficient thickness to provide the required mechanical strength for the particular application. An advantage of a thinner membrane is that more rapid separation times can be achieved. Moreover, a thinner membrane, requires less processing to remove soluble entities from the membrane.

The polymeric membrane of the first aspect of the invention may be a crosslinked or non-crosslinked polymeric membrane. Preferably, the polymeric membrane is a crosslinked polymer membrane.

Preferably, the thickness of the membrane components making up the membrane is in a range of about 0.01 mm to 0.5 mm.

The polymeric membrane system of the first aspect of the invention has particular (but not exclusive) application to thin membranes. Preferably, in this case, the thickness of the membrane components making up the membrane is in a range of about 0.01 to 0.1 mm, more preferably about 0.03 to 0.09 mm.

In a second aspect, the present invention provides polymeric system according to the first aspect wherein the polymeric membrane is an ultra-thin membrane.

The polymeric membrane of the polymeric membrane system of the present invention may be formed from any crosslinked or non-crosslinked polymer conventionally used to prepare membranes. Preferably, the membrane is a hydrophilic membrane.

The membrane may be any gel-forming polymer. The membrane may be an electrophoretic gel. Examples of suitable polymers include, but are not limited to polyacrylamide gels and poly HEMA with EGDMA.

The substrate is preferably formed from a material that is relatively inert, has good wet strength and does not bind to the substance undergoing separation (eg proteins). The substrate has a plurality of interstitial gaps therein. Preferably the size of the interstitial gaps is no greater than the thickness of the substrate. The substrate may be woven or non-woven. The substrate may be a woven or non-woven material or a textile. The substrate is in the form of a sheet, web, or any other appropriate form.

The substrate may be formed from any material that is conventionally used as a membrane support. Non-limiting examples of suitable materials for use as substrates include, but are not limited to polyvinyl alcohol, polyethyleneteraphthalate (PET), nylon and fiberglass, cellulose, cellulose derivatives, or any other suitable substrates. Preferably the substrate is hydrophilic nature in the case of aqueous solvent systems. In the case of an organic solvent system, the substrate is preferably possesses a similar hydrophilicity to the solvent used.

An example of a hydrophilic substrate material is polyvinyl alcohol. Polyvinyl alcohol paper has been found to be a suitable substrate. It is available in several different weights and thicknesses and may be used as the substrate without pre-treatment.

An example of a suitable substrate is Papylon, the trade name for the PVA1 paper (Sansho Corporation, The $2^{nd}$ Kitahama Building 1-29, Kitaham-Higashi, Chuoh-Ku, Osaka, Japan, Ph: 06 6941 7895). Papylon has both excellent wet and dry strengths and has a very regular flat structure. We found that the two best performing were BFN No 2, which has a weight of 24.5 g/m$^2$ and a thickness of 0.092 mm and BFN No. 3, which has a weight of 36.3 g/m$^2$ and a thickness of 0.130 mm. The BFN No. 2 performed quite adequately and we used it to perform most of the tests described below.

A further example of a suitable substrate is heat bonded polyethyleneterephthalate. Because of its hydrophobic nature, PET requires some pre-treatment to enable better wetting of the surface by the aqueous monomer solution. The surface may be pretreated with a non-ionic surfactant, which renders the PET more hydrophilic while not introducing any charged groups into the system.

It is, however, preferable that no pre-treatment of the substrate is necessary.

In a third aspect, the present invention provides a method for the production of a polymeric membrane system of the first aspect, wherein a substrate having a plurality of interstitial gaps is contacted with at least one membrane-forming monomer and at least one crosslinker and subjecting the at least one monomer to polymerization.

Preferably, the method of the third aspect of the invention includes a treatment step to remove any soluble entities, for example, residual monomer, in the formed polymer to a point where the soluble entity (entities) are undetectable. In the case of aqueous system, water-soluble entities are not detectable. In the case of organic systems, organic soluble entities are not detectable. Most preferably, the system has no detectable residual soluble monomer(s), oligomers, initiator, etc.

The treatment may be one or more washing steps. As already mentioned above, the polymeric membrane system of the present invention is such that very thin membranes may be achieved. In the case where a very thin membrane is formed (eg an ultrathin membrane) as little as one wash may be required to render residual soluble entities to undetectable levels. Preferably the washing process is automated and the washing continued until there is no detectable soluble entities. This can optionally be computer controlled, driven by a feedback loop via an on-line detection system.

Residual entities, including monomer(s) can be measured by any of the appropriate well-established methods (see Reviews in Environmental Health, 9(4), 1991, 215–228), including High Performance Liquid Chromatography (HPLC), Capillary Electrophoresis (CE) and various bromination methods.

Preferably, the substrate used in the method of the invention is subjected to a degas treatment before being contacted with the monomer(s).

The membrane system may be made by a batch method or a continuous method.

In the batch method, the monomer(s) is applied to the substrate, which may be, for example, in the form of a sheet, and the monomer(s) subjected to polymerization. The monomer(s) may be applied by simply dipping the substrate into a monomer solution. Preferably dipping of the substrate into the monomer solution takes place at a controlled speed to ensure a consistent coating of the monomer solution.

Polymerization of the monomer(s) may be achieved by any method that is suitable for the monomer(s) used. Initiation of the polymerization may be conducted by a photo, redox or thermal methods.

In the case of a photopolymerization, the substrate may be coated with the monomer(s) and photoinitiator(s) polymerised by being irradiated for a predetermined time.

With thermal polymerization, the substrate may be coated with the monomer(s) and optionally an initiator (eg APS) then heated to a temperature at which polymerization occurs.

In the case of redox polymerization, a co-initiator (eg TEMED) may be applied to the substrate (eg by spraying), followed by application of the monomer(s) with an initiator, (eg APS). The substrates may then transferred into the reaction chamber for the polymerization.

As already mentioned, the polymeric membrane system of the present invention may be prepared by a continuous method, in which case, the substrate, in a continuous form (eg a continuous web) is continuously contacted with a monomer(s) followed by polymerization of the monomer(s).

Where appropriate, the polymerization methods used for the continuous method may be those discussed above in relation to the batch method.

Preferably, the substrate is degassed before being contacted with the monomer. We have found that with degassing treatment, the polymerization gave a lower induction period and the resultant membrane gave lower endosmosis.

Thickening agents have been used to alter the viscosity of the monomer composition before applying the monomer to the substrate. We however found that when we used un-thickened monomer solution and polymerized it, the resultant material appeared no different from the wet substrate. Indeed, we initially believed that the polymerization had been unsuccessful. We had expected to get a membrane that looked similar to the membranes in the prior art with a glossy appearance. However, on closer inspection there appeared to be a polymeric film on the substrate. The membranes were found to be water-resistant and had a defined pore size.

Depending on the application, it may be necessary to add a thickening agent to the monomer solution.

For the purposes of further illustrating the present invention, we will now describe the invention in reference to polyacrylamide gels as the polymeric gel used in the polymeric membrane system, however, it will be clear to the skilled reader that any monomer system that is capable of forming a membrane may be used with the present invention.

The crosslinked polymer gel may be prepared from monomer(s) having the formula $H_2C=CR^5-CO-NR^3R^4$ where $R^3$, $R^4$ and $R^5$ are each independently H or alkyl optionally monosubstituted by, for example, OH or $C(O)$ $CH_2C(O)$ $CH_3$. Examples of monomers include acrylamide, acrylamide derivatives or acrylamide substitutes known to the art such as N,N-dimethylacrylamide, methacrylamide, methyloylacrylamide, propylacrylamide, dipropyl acrylamide, isopropyl acrylamide, diisopropyl acrylamide, lactyl acrylamide, methoxyacrylamide and mixtures thereof. Preferably the monomer is acrylamide.

These polyacrylamide gel may be produced by copolymerization of the momomer(s) with a conventional crosslinking agent such as N,N'-methylene bisacrylamide, otherwise known as BIS. Other known crosslinking agents include but not limited to the following ethylene glycol diacrylate, dihydroxy ethylene-bisacrylamide (DHEBA), N,N'propylenebisacrylamide, diacrylamide dimethylether, 1,2-diacrylamide ethyleneglycol, ethyleneureabisacrylamide, N,N'bisacrylylcystamine and bisacrylamide methylether (BAME). As for BIS, the double bonds of these crosslinking agents are of the same type.

The crosslinked polymer gel may be produced by using the monomer with the following formula:

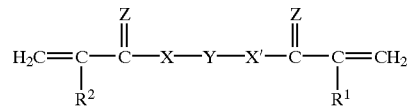

wherein

X and X' are independently selected from the group consisting of —O—, —S— and —NR—, where R is H, alkyl or cycloalkyl, $R^1,R^2$ is a $C_1$–$C_4$ alkyl group, Y is an optionally substituted non-aromatic divalent linking group, and Z is O or S. Such crosslinked polymers are described in International Patent Application PCT/AU97/00437, the whole disclosure of which is incorporated herein by reference.

The crosslinker may be a combination of crosslinkers at least one of which has at least three crosslinkable functional groups, wherein at least one of the crosslinkable functional groups is the group $CH_2=C(R)-CO-$, where R is H or optionally substituted alkyl, as described in PCT/AU00/00238 the disclosure of which is incorporated herein by reference. The crosslinker having at least three crosslinkable functional groups is a compound of Formula I or Formula II

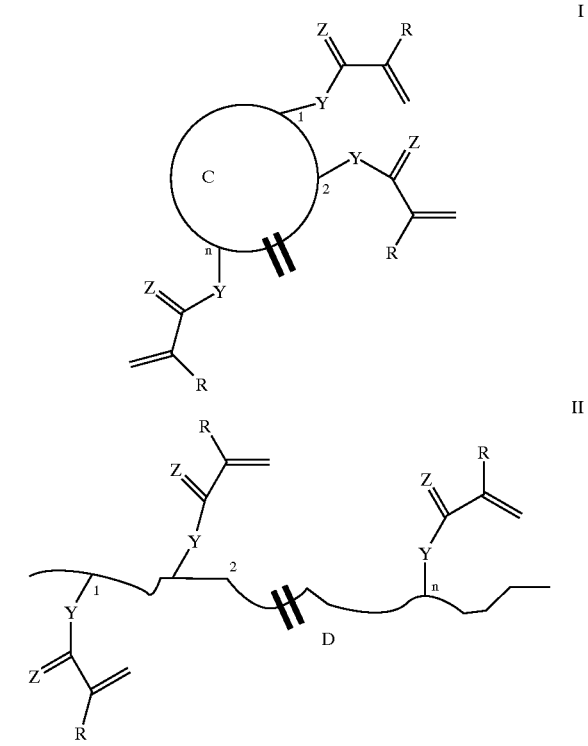

wherein, in Formula I:

C represents a ring structure of the crosslinker molecule which is connected with at least 3 functional groups —Y—CZC(R)=CH$_2$ which functional groups may be the same or different;

Y in each functional group is independently selected from single bond, N, O or S;

Z in each functional group is independently selected from O or S; or Z may be two hydrogens, a hydrogen an optionally substituted alkyl, or two optionally substituted alkyl groups, and R in each functional group may be the same or different and selected from hydrogen or optionally substituted alkyl; and In Formula II:

D represents a backbone chain of the crosslinker which is connected with at least three functional groups —Y—CZC(R)=CH$_2$ which functional groups are the same or different;

Y in each functional group is the same or different and selected from the group consisting of a single bond, N, O or S;

Z in each functional group may be the same or different and selected from O or S; and R in each functional group is the same or different and selected from hydrogen or optionally substituted alkyl.

As used herein the term "on-aromatic hydrocarbyl group" means any divalent group comprising carbon and hydrogen which does not include an aromatic or heteroaromatic ring.

As used herein the term "alkylene", used either alone or in compound words such as "oxyalkylene", "carbonylalkylene" denotes straight chain and branched $C_{1-10}$ alkylene groups. Examples include methylene, ethylene, propylene, isopropylene, butylene, isobutylene, sec-butylene, pentylene, isopentylene, sec-pentylene, 1,2- dimethylpropylene, 1,1-dimethylpropylene, hexylene, 4-methylpentylene, 1-methylpentylene, 3-methylpentylene, 1,1-dimethylbutylene, 2,2-dimethylbutylene, 3,3-dimethylbutylene, 1,2-dimethylbutylene, 1,3-dimethylbutylene, 1,2,2-trimethylpropylene, 1,1,2-trimethylpropylene, heptylene, 5-methylhexylene, 1-methylhexylene, 2,2-dimethylpentylene, 3,3-dimethylpentylene, 4,4-dimethylpentylene, 1,2-dimethylpentylene, 1,3-dimethylpentylene, 1,4-dimethylpentylene, 1,2,3-trimethylbutyl, 1,1,2-trimethylbutylene and the like.

The term "cycloalkylene", used alone or in compound words such as "alkylenecycloalkylene" denotes divalent cyclic $C_{3-7}$ alkyl groups. Examples include cyclopropyl, cyclobutyl, cyclopentyl and cycloheptyl.

The term "heterocyclyl" as used alone or in compound names such as "alkyleneheterocyclyl" denotes 5 or 6 membered heterocyclic rings. Examples of 5 or 6 membered heterocyclic rings include pyrrolidine, imidazolidine, pyrazolidine, thiazolidine, isothiazolidine, oxazolidine, piperidine and piperazine.

In this specification the term "optionally substituted" means that a group may or may not be further substituted with one or more groups selected from alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenacyl, alkynylacyl, acylamino, diacylamino, acyloxy, alkylsulphonyloxy, heterocyclyl, heterocycloxy, heterocyclamino, haloheterocyclyl, alkylsulphenyl, carboalkoxy, alkylthio, acylthio, phosphorous-containing groups such as phosphono and phosphinyl, and groups of the formula

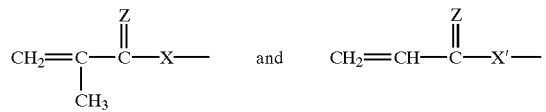

where X, X' and Z are as defined above.

The term "alkyl", used either alone or in compound words such as "haloalkyl" or "alkylthio", denotes straight chain or branched $C_{1-6}$ alkyl groups. Examples include methyl, ethyl, propyl, isopropyl and the like.

The term "alkoxy" denotes straight chain or branched alkoxy, preferably $C_{1-10}$ alkoxy. Examples include methoxy, ethoxy, n-propoxy, isopropoxy and the different butoxy isomers.

The term "alkenyl" denotes groups formed from straight chain, branched or mono- or poly-cyclic alkenes including ethylenically mono- or poly-unsaturated alkyl or cycloalkyl groups as previously defined, preferably $C_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cyclooctatetraenyl.

The term "halogen" denotes fluorine, chlorine, bromine or iodine, preferably chlorine or fluorine.

The term "acyl" used either alone or in compound words such as "acyloxy", "acylthio", "acylamino" or diacylamino"

denotes carbamoyl, aliphatic acyl group and acyl group containing a heterocyclic ring which is referred to as heterocyclic acyl, preferably $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopropylcarbonyl cyclobutylcarbonyl, cyclopentylcarbonyl or cyclohexylcarbonyl; alkylsulfonyl, such as methylsulfonyl or ethylsulfonyl; alkoxysulfonyl, such as methoxysulfonyl or ethoxysulfonyl; heterocyclylcarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

Free radical polymerization of vinyl monomer(s) can be initiated using a variety of different initiating systems. One of the chemical polymerizations is performed using ammonium persulfate (APS) as the initiator and N,N,N'N'-tetramethylenediamine (TEMED) as the activator.

An advantage of using photo-polymerization is that very high conversions of monomer to polymer can be achieved. Photo-polymerization systems are theoretically well suited to this application as radicals are continuously produced as long as light is being absorbed (Caglio, S.; Righetti, P. G. *Electrophoresis* 1993, 14, 554–558). This is in contrast to the persulphate redox polymerization where, once the initiators have been mixed together, there is a limited time for which they can be used and production of radicals is continuous. Whereas for photo-polymerization systems, reaction does not occur until it is hit with a source of light (Chiari, M.; Micheletti, C.; Righetti, P. G.; Poli, G. J. *Chromatography* 1992, 598, 287–297).

Photoinitiator systems are usually composed of a dye (which absorbs light energy) and an oxidiser/reducer couple (which produce the free radicals). A selection of photoinitiator systems were used, including the traditionally used methylene blue (MB)/sodium toluene sulfinate (STS)/ and diphenyliodonium chloride (DPIC). Good results were obtained by the use of riboflavin 5'-monophosphate sodium salt dihydrate (RMN—Na)/STS and DPIC system (Structures of photo-initiating system—see FIG. 2).

The wavelengths via which the dye absorbs incident light were measured on a UV spectrophotometer to determine the most appropriate light source (See FIG. 3). The main features of the absorption profile are the two areas where riboflavin strongly absorbs light energy, one around 380 nm (UV) and one further up at around 450 nm (more in the visible light range). This suggests that the reaction to form the initiating radicals can occur using either UV radiation or visible light, such as produced from a fluorescent lamp. The intensity of the light also has a bearing on the rate of the reaction, the more intense the light, the faster the rate of reaction. Both fluorescent (produces visible light) and UV lamps have been thoroughly tested during the course of our investigation. The particular application might determine the light system used.

Without the present invention being bound by theory, it is generally believed that the polyacrylamide formed from photo-polymerization contains chemically bound sulfinates and DPIC residues. These are both non-acidic and the oxidizing power of the residues and unreacted species is considerably lower than the persulfate chemical polymerization currently used (Lyubimova, T.; Caglio, S.; Gelfi, C.; Righetti, P. G.; Rabilloud, T. *Electrophoresis* 1993, 14, 40–50; Rabilloud, T.; Vincon, M.; Garin, J. *Electrophoresis* 1995, 16(8), 1414–1422).

The concentration of the photoinitiator system used for the polymerization is preferably kept low as practically possible. This will minimize the chance of the initiator residues contained within the polymer network interfering in any way with the use of the membrane.

Whilst the polymerization can be conducted under any atmosphere, it is preferable to have an oxygen-free environment. The presence of oxygen in the polymerization zone will have the effect of slowing down the reaction and delaying gel time, as oxygen acts as a retarder/inhibitor in the photoinitiated system (Margerum, J. D.; Lackner, A. M.; Little, M. J.; Petrusis, C. T. *J. Phys. Chem.* 1971, 75, 3066–3074; Gelfi, C.; De Besi, P.; Alloni, A.; Righetti, P. G.; Lyubimova, T.; Briskman, V. A. *J. Chromatography* 1992, 598, 277–285.). Therefore the amount of oxygen is preferably controlled in the production process.

Preferably, greater than 95% more preferably greater than 99% conversion is achieved in the method of the present invention. Such high conversions can be obtained by controlling the reaction conditions carefully. It is particularly important to maintain the oxygen concentration as low as possible. An atmosphere of an inert gas (eg nitrogen or argon) should blanket over both the coater and the polymerization zones. This will allow polymerization to occur at peak efficiency, and ensure that the conversion will be pushed as high as possible.

The following embodiments are provided for the purpose of further illustrating the present invention but in no way are to be taken as limiting the present invention.

EMBODIMENTS OF THE INVENTION

Batch Method—General methodology

An ultra thin membrane (UTM) is produced by a batch method. This process comprises three main steps, application of monomer solution onto the substrate, polymerization and membrane washing. Dipping the substrate in the monomer solution is carried out at a controlled speed to ensure even monomer application.

Initiation of the polymerization can be conducted by photo, redox or thermal method. In the photo polymerization, the substrates coated with the monomer(s) and photo initiators were transferred into an irradiation chamber and polymerised for a set time before moving out of the chamber for the next step. In the thermal polymerization, the substrate is coated with the monomers and APS are transferred into the thermal chamber where the temperature and humidity are controlled. In the redox polymerization, the substrates are transferred into a spray chamber where co-initiator, TEMED is sprayed on the substrate, followed by the spray of a monomer solution with the initiator, APS. The substrates are then transferred into the reaction chamber for the polymerization. The step after polymerization is the washing where all the water-soluble components including any residue monomers are washed away until it is not detectable. An on-line detector examines this. Preferably the washing process is automated and the washing continued until there is no detectable soluble entities. This can optionally be computer controlled, driven by a feedback loop via an on-line detection system.

EXAMPLE 1

Batch System Using Photo Initiation

Figure 1:
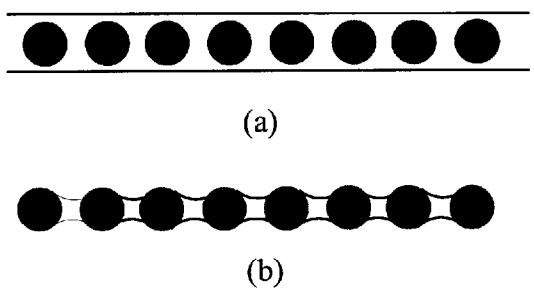
FIG. 1 is a schematic representation of: (a) conventional membrane made between two glass plates. (b) novel membrane made by the process described in this invention, where the circles represent the fibrils of the substrate.
Figure 2:
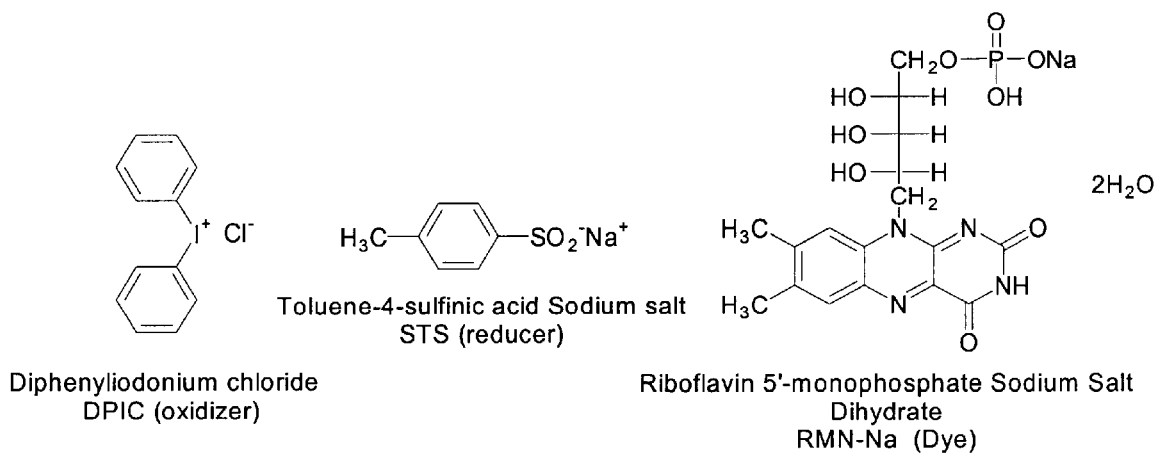
FIG. 2 shows the chemical structures of photo-initiating system that may be used to form a membrane in accordance with the present invention.
Figure 3:
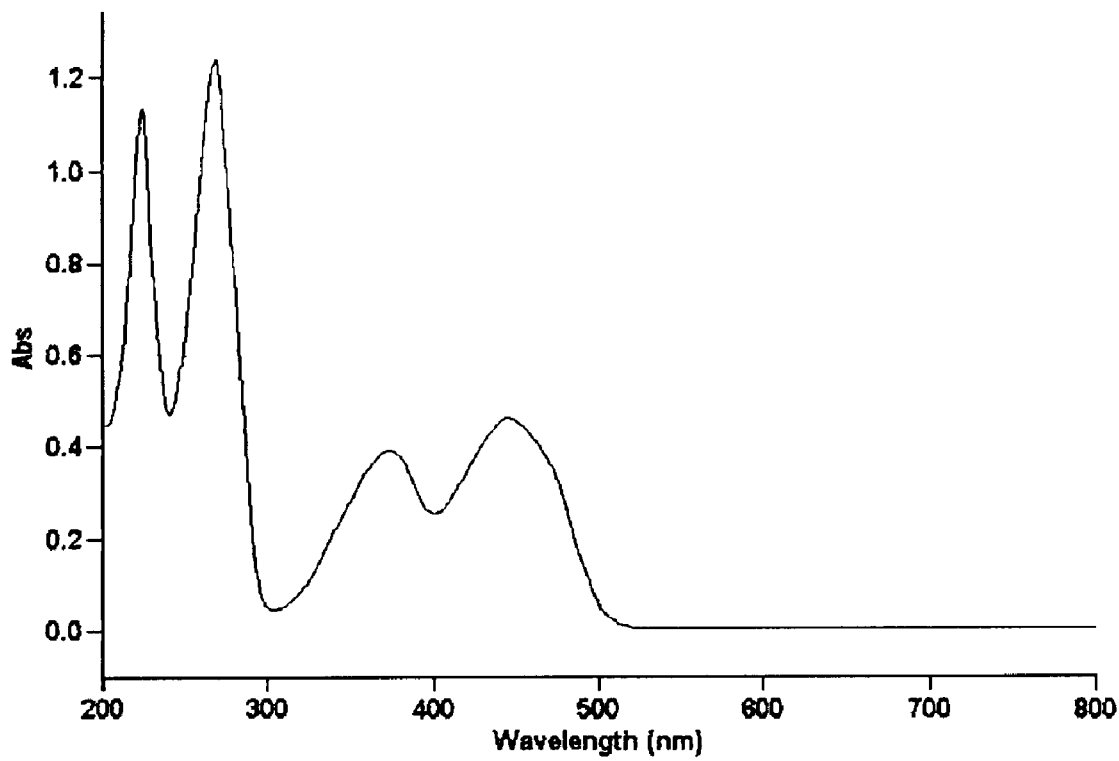
FIG. 3 is a graph of Absorbance vs wavelength (nm) for Riboflavin 5'-Monophosphate Sodium Salt Dihydrate (RMN—Na) dye.
Figure 4:
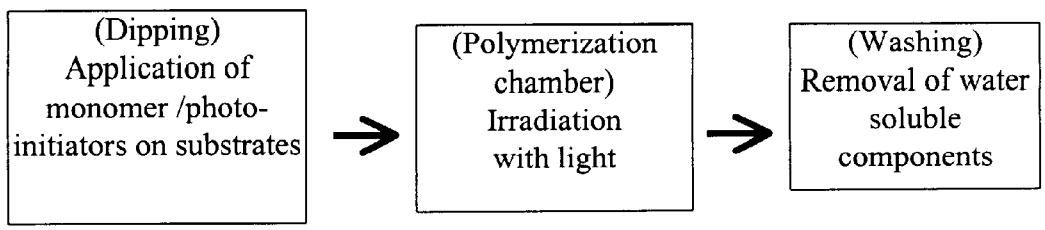
FIG. 4 is a schematic diagram showing a membrane batch process with photo polymerization method.

An embodiment of a batch production line designed to produce a membrane of the present invention is shown in FIG. 4.

In the step of dipping, monomer(s) solution with photo-initiator, Riboflavin/STS/DPIC, is applied to the substrates by dipping the substrates in the solution at a controlled speed. The substrates is then transfered into a polymerization chamber where irradiation is given for a fixed time. After polymerization the membrane is transfered again to the washing step to remove all remaining the water soluble components including acrylamide residue.

EXAMPLE 2

Batch System Using Thermal Initiation

Figure 5:
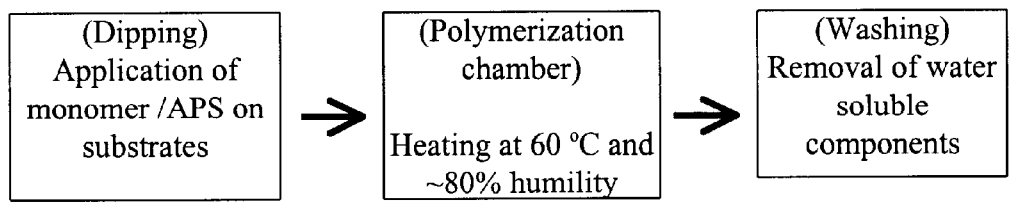
FIG. 5 is a schematic diagram showing a membrane batch process with thermal polymerization method.

An embodiment of the batch production line designed to produce a membrane of the present invention is show in FIG. 5.

In the step of dipping, monomer solution with a thermal-initiator, APS, is applied to the substrates by dipping the substrates in the solution at a controlled speed. The substrates is then transfered into a polymerization chamber where the temperature is controlled at 60° C. and the huminity is controlled to at least~80%. After polymerization for 60 min, the membrane is transfered again to the washing step to remove all remaining water soluble entities including acrylamide residue.

EXAMPLE 3

Batch System Using Redox Initiation

Figure 6:
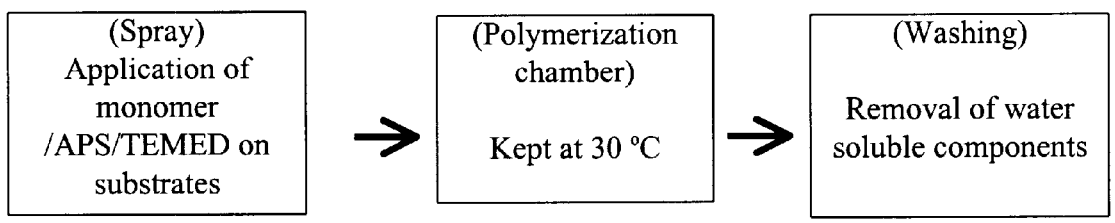
FIG. 6 is a schematic diagram showing the components of a continuous production line in accordance with an embodiment of the invention.

An embodiment of the batch production line designed to produce a membrane of the present invention is show in FIG. 6.

In the step of spray, A coinitiator, TEMED solution is sprayed on to the substrates followed by the spray of another solution mixture with the monomer and initiator, APS. The substrates is then transfered into a polymerization chamber where the temperature is kept at 30° C. After polymerization for 60 min, the membrane is transfered to the washing step to remove all remaining the water soluble components including acrylamide residue.

EXAMPLE 4

Degassing of the Substrates

A degassing unit was positioned before the process of a continues line as described in Example 1 or Example 2 to 3. The degas unit used is similar to the one described in example 6. The polymerization process was monitored by a temperature profile and the membrane product after the washing step was used to exam the quality. It was found that with degassing treatment, the polymerization gave lower induction period and the membrane gave lower endosmosis during the Gradiflow tests.

EXAMPLE 5

Continuous Production Line

Figure 7:
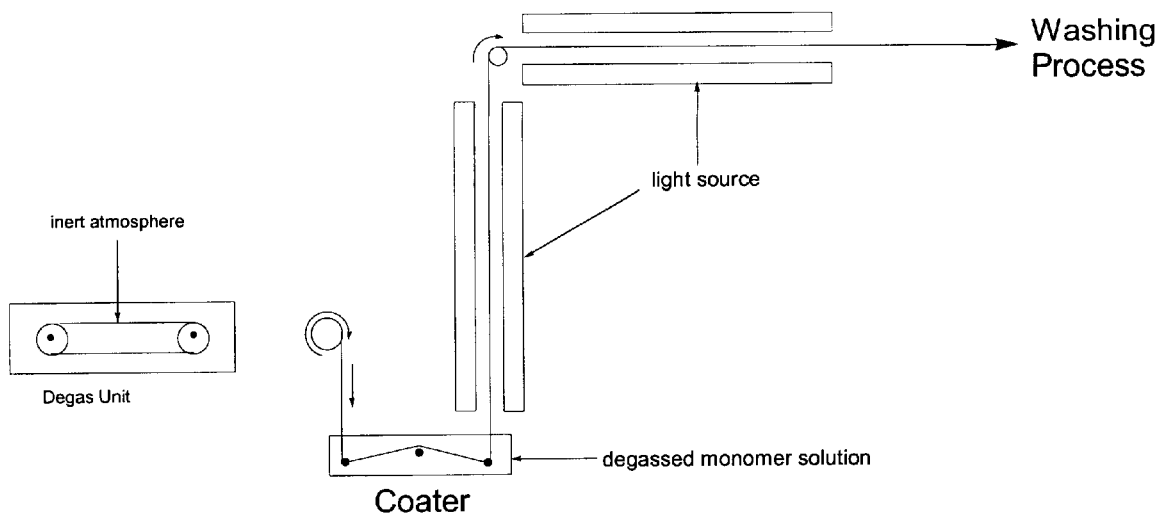
FIG. 7 is a schematic diagram of a preferred embodiment of a coater configuration: (a) side view and (b) view from above.

An embodiment of a continuous production line designed to produce a membrane of the present invention is shown in FIG. 7. The substrate is fed through a coater containing degassed monomer solution. The coated substrates are passed between light sources in an initial polymerization step and then between light sources for further polymerization. The process is continuous, which lends itself more to a higher production rate. The process is also designed to be less labour intensive, push the reaction to higher conversions, have greater control over the reaction conditions and remove the chances of direct exposure of the operator to monomer(s) solution.

Coater

Figure 8:
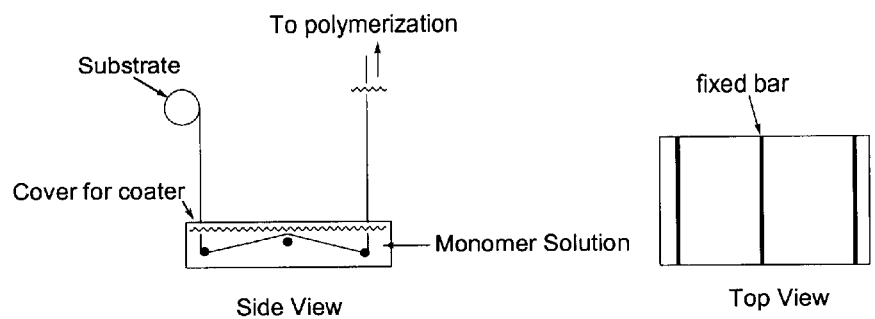
FIG. 8 is a schematic diagram of a membrane batch process with redox polymerization method

The requirements of the coater included: high efficiency, excellent reproducibility, low maintenance and ease of cleaning. One of the best results was obtained by pulling the substrate through a bath of the monomer solution, as depicted in FIG. 8.

The coater may be a flat bath containing several fixed bars, which are placed at regular intervals along the length of the bath. In this embodiment, the coater contained three bars, slightly offset from each other (as seen in FIG. 8). The substrate is threaded around the bars, and provides a shearing action, ensuring any bubbles in the solution are dislodged. Each bar should be placed at a position as to be totally submerged within the monomer solution at all times.

In this preferred embodiment, the Coater had the following important features: no viscosity control required; substrate dragged through solution at a constant controlled rate and monomer solution degassed normally.

Figure 9:
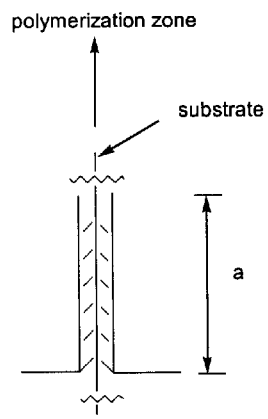
FIG. 9 is a schematic diagram of an arrangement for protecting monomer solution from light where a is as short as necessary.

The monomer solution in the coater needs to be protected from all sources of light, including the polymerization lights. This was accomplished by covering the top of the coater with a lightproof cover, therefore excluding as much light as possible from the solution. This can be observed in FIG. 9, with the substrate coming through a slit in the lid.

Care was taken to ensure that the slit was as small as possible and aligned correctly with the bars in the coater. In addition, the distance marked "a", on FIG. 9, was selected to be short as possible. The best configuration would have the shortest time between addition of the monomer solution in the coater and its exposure to the light.

The coater can be any one known to those skilled in the art.

EXAMPLE 6

Substrate Degas Unit

One option for even tighter control over the reaction conditions is to include facilities for degassing the substrate. Referring to FIG. 7, this unit is best designed as an add-on unit associated with cover, which could work independently of the production unit.

EXAMPLE 7

Illumination Conditions

In this particular embodiment, the unit contained two 36 W fluorescent lamps, placed at a distance of 100 mm from the monomer treated substrate. The lamps were approximately 1240 mm long. A possible configuration for the production unit would have the lights vertically aligned. This allows for the dissipation of the heat generated by the lamps to be pushed upwards and circulated away from the substrate. The polyacrylamide layer is formed evenly along the width of the substrate. The membrane is washed until all the soluble components including any residue monomer(s) are washed away until it is not detectable. Preferably the washing process is automated and the washing continued until there is no detectable soluble entities. This can optionally be computer controlled, driven by a feedback loop via an on-line detection system.

EXAMPLE 8

Movement of Substrate through the Production Unit

The movement of the substrate through the unit is preferably controlled very carefully. The rate at which the substrate is moved through the production unit should be constant and reproducible over extended periods of time. Both the application of the monomer(s) and the conversion of the monomer to polymer are dependent on the speed of the process. If the rate through the unit is too high, less monomer solution will be applied, producing variations in the membrane thickness. In addition, the amount of time the monomer solution is irradiated will be reduced and consequently the conversion lowered. Conversely, if the process goes too slow, additional problems associated with the membrane thickness and drying out of the membrane could occur.

The rollers will also probably have to have some provision for cleaning, as they will be exposed to monomer solution and could easily get fouled.

EXAMPLE 9

Method for Measuring the Conversion after Polymerization

We have developed an accurate method for measuring the concentration of unreacted monomer(s) in the polyacrylamide gels. The method utilizes the direct relationship between the intensity of a HPLC peak and the concentration of the compound in solution. Therefore a standard curve can be generated and the concentration of an unknown experimental sample can be accurately determined.

Figure 10:
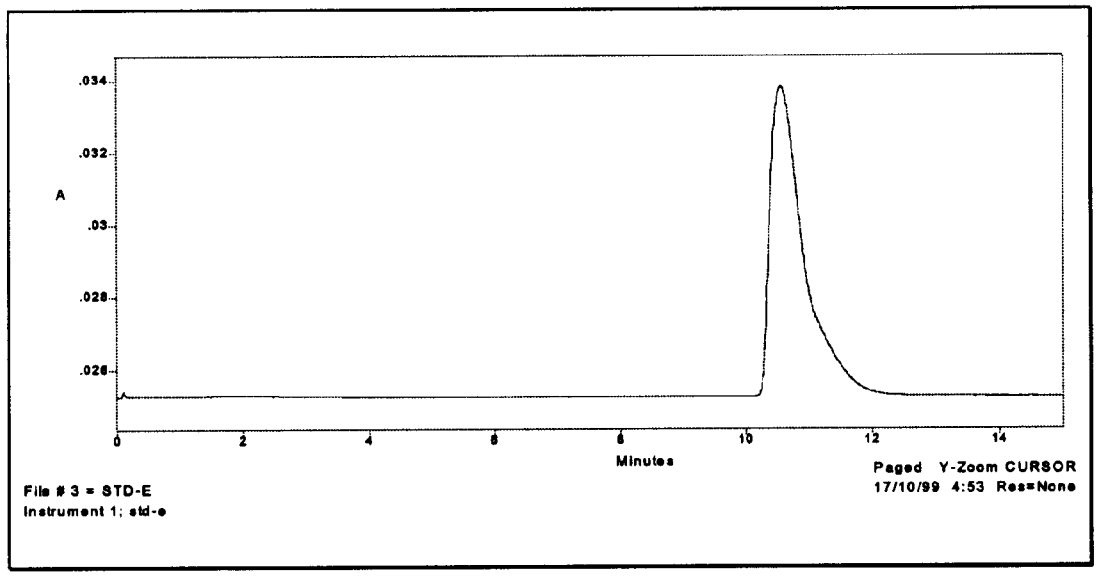
FIG. 10 is an HPLC curve for a sample solution.
Figure 11:
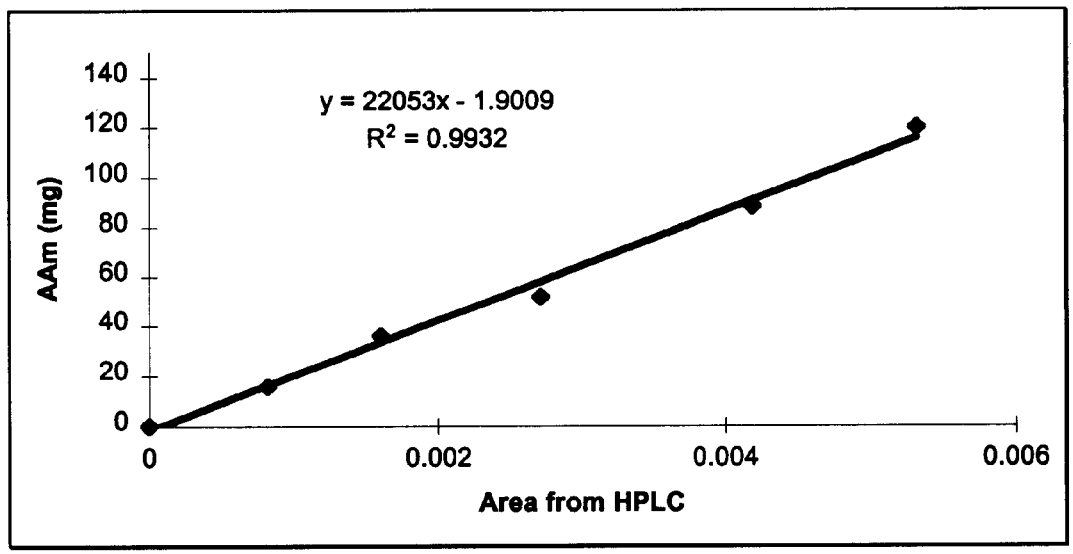
FIG. 11 is a standard curve of the amount of acrylamide (mg) vs area of peak.

Generation of a Standard Curve
1. In five 50 ml standard flasks, 15.8, 36.1, 52.0, 88.1 and 119.6 mg of acrylamide was respectively added.
2. Each flask was made to 50 ml using methanol.
3. 50 μl of the sample from each flask was injected into a High Performance Column Chromatography (HPLC). The condition for the HPLC used:
   Column: Phenomenx column, Spherex/5/C18, size: 250×10 Micron
   Flow rate: 1 ml/min
   Eluent solvent: Methanol
   Run Time: 30 minutes
   Detector: UV detector at 254 nm
4. After a 30 minute run, a peak due to the absorption of the acrylamide monomer was observed from HPLC curve. A typical curve is shown in FIG. 10—HPLC curve of sample solution.
5. The area of the monomer curve was integrated for each sample and a standard curve of the amount of monomer in the 50 ml flask versus area of monomer curve was plotted. (FIG. 11—Standard curve of amount of acrylamide (mg) vs Area of peak) is a standard curve made from the 5 samples described in 2.

Standard Method for Measuring Monomer Concentration in Experimental Samples
1. A piece of membrane or a gel sample (about 4 to 10 g) is weighed and crushed into a powder using a spatula.
2. The powder is washed with methanol (10 ml each time, 4 times) and the washings transferred into a 50 ml standard flask and the solution is made up to 50 ml with methanol.
3. 50 μl of the sample from the flask is injected into HPLC and during a 30 minute run a monomer peak was observed from the HPLC.
4. The area of the monomer peak is integrated and the amount of the monomer in the 50 ml methanol solution (equal to the amount extracted from the sample) was calculated by using the standard curve from FIG. 11.
5. The conversion is calculated based on the amount of monomer used to produce that amount of sample and the amount of residue monomers measured from HPLC:
6.

$$\text{Conversion} = \frac{\text{TotalMonomer (mg)} - \text{MonomerResidue (mg)}}{\text{TotalMonomer (mg)}} \times 100\%$$

EXAMPLE 10

Measurement of the Conversion of Monomer to Polymer to Form Membrane Initiated Via Photopolymerization The conversion of monomer to polymer was measured by a HPLC technique. The intensity of the acrylamide signal from the HPLC chromatogram was found to be directly proportional to its concentration in solution, enabling a standard graph to be produced and quantification of the conversion obtained. This was compared to the polymerization initiated with the redox system.

Figure 12:
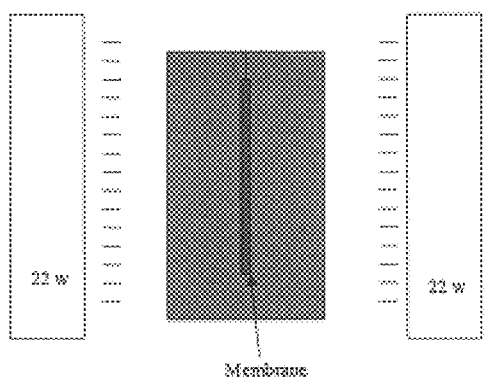
FIG. 12 is a schematic representation of a setup used for measuring conversion of acrylamide to polyacrylamide.

Membranes with different irradiation times were produced using a small experimental sized set-up, as shown in FIG. 12 (Experimental set-up used for measuring conversion of acrylamide to polyacrylamide).

The formulation of the monomer solution was 30/10 (%T/%C) and PET was used as the substrate. The monomer solution was degassed with Ar and the oxygen concentration in the solution was measured to be less than 1%. The solution was covered/protected with an Ar atmosphere, and the PET paper dipped into the monomer solution. The substrate was immediately transferred to a 1000 ml beaker and irradiated between two 22W fluorescent lamps at a distance of 100 mm either side of the beaker.

Figure 13:
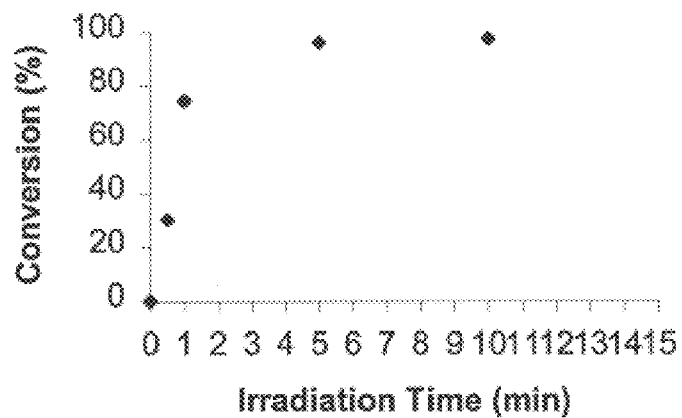
FIG. 13 is a graph of percentage conversion of monomer to polymer vs irradiation time as measured by HPLC.

Experiments were conducted at varying times of irradiation and the unreacted monomer from the membrane sheets were extracted with methanol several times and the conversion of the polymerization determined by HPLC method as described in Example 9. FIG. 13 (Percentage conversion as measured by HPLC) shows the conversion from these tests. It was found that after 3 minutes irradiation, the conversion was already more than 90%.

EXAMPLE 11

A membrane produced by photopolymerization according to Example 6, after 10 minutes irradiation, had a conversion greater than 99%. This membrane was subjected to one aqueous wash and the residual monomer level was again measured using HPLC. No residual monomer was detectable.

EXAMPLE 12

Membrane Performance Poly (Vinyl Alcohol) Substrate Using 20/5 (%T,%C) Formulation The membranes produced under photo-polymerization conditions were tested for their protein separation qualities using a Gradiflow™ Model Number BF-200 instrument (available from Gradipore Limited).

A membrane with a 20/5 (%T, %C) formulation was made using a photoinitiation system and the substrate, a PVA1 sheet (BFN 3). The substrate was dipped through the solution immediately before irradiating the sample in a beaker for 5 minutes.

The formed membrane was washed, cut to the specific size and tested with the Gradiflow™ instrument. The buffer used was a 40 mM solution of TB (Tris-Borate) and 10 ml of protein stock solution (made from the mixture of Bovine Serum Albumin (BSA, 0.20 mg/ml) and Ovalbumin (OA, 0.67 mg/ml) in TB buffer) was loaded into the upstream before the test. The separation was run for 30 minutes and samples (100 μl) were taken at 10 minute intervals from both the up and downstream. To each of these samples, 20 μl sample buffer (containing 40% sucrose and 0.05% Bromophenyl Blue in TB buffer, ratio of sample to buffer as 5:1) was added. 20 μl of each sample was then loaded to a gel well and a standard protein marker was also loaded into one well as a reference. The electrophoresis was then performed. The buffer used was 80 mM TB and the electrophoresis condition was at 200 V, 500 mA for 1.5 hours. The gel was then stained with blue dye overnight followed by washing with 6% acetic acid.

Figure 14:
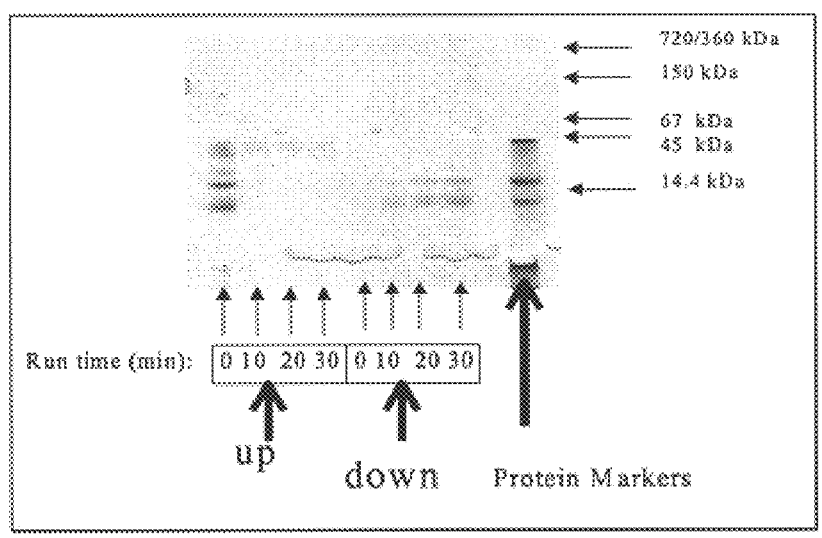
FIG. 14 shows the electrophoresis results of membrane performance test using photoinitiation and PVAI as described in Example 12.

The results from the electrophoresis after Gradiflow™ test are shown in FIG. 14 (Results from the Gradiflow experiment using photoinitiation and PVA1 as a substrate). It is clearly observed that proteins with sizes less than 150 kDa went through from the upstream to the downstream. The membranes produced from the continuous model system have a typical 100 kDa cut-off.

EXAMPLE 13

Figure 15:
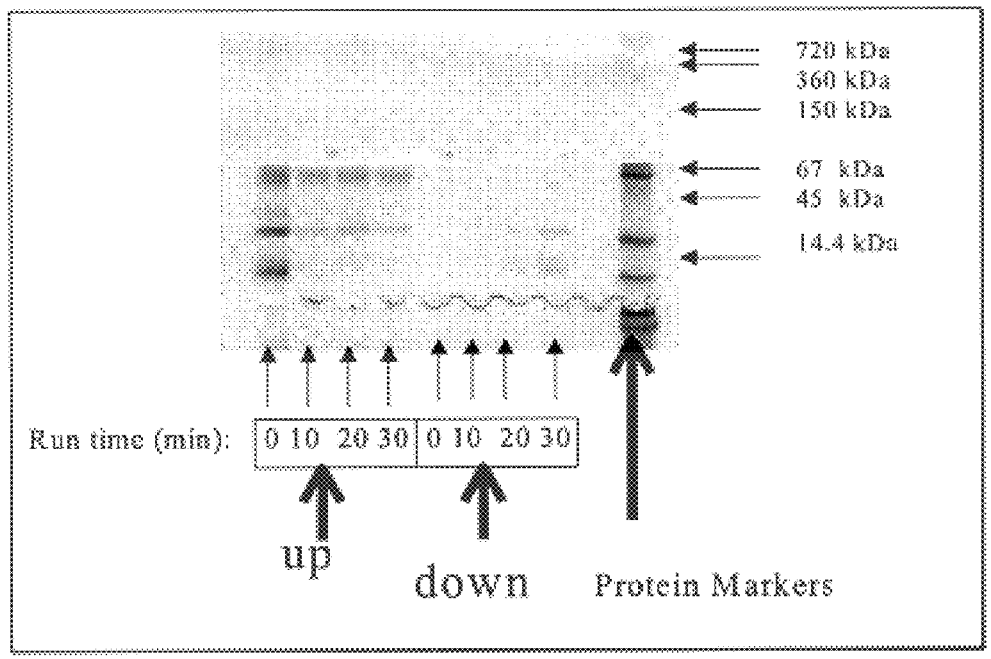
FIG. 15 shows the electrophoresis results from a 50 kDa membrane using photoinitiation and PVAI substrate as described in Example 13.

Membrane Performance: Poly (Vinyl Alcohol) Substrate Using 30/10 (%T, %C) (50 kDa) formulation Using a Gradiflow™ unit, a test was performed on the membrane and the electrophoresis results are shown in FIG. 15 (Electrophoresis results from 50 kDa membrane using photoinitiation and PVA1 ). It is observed from this result that proteins with sizes less than 67 kDa went through from the upstream to downstream.

EXAMPLE 14

Figure 16:
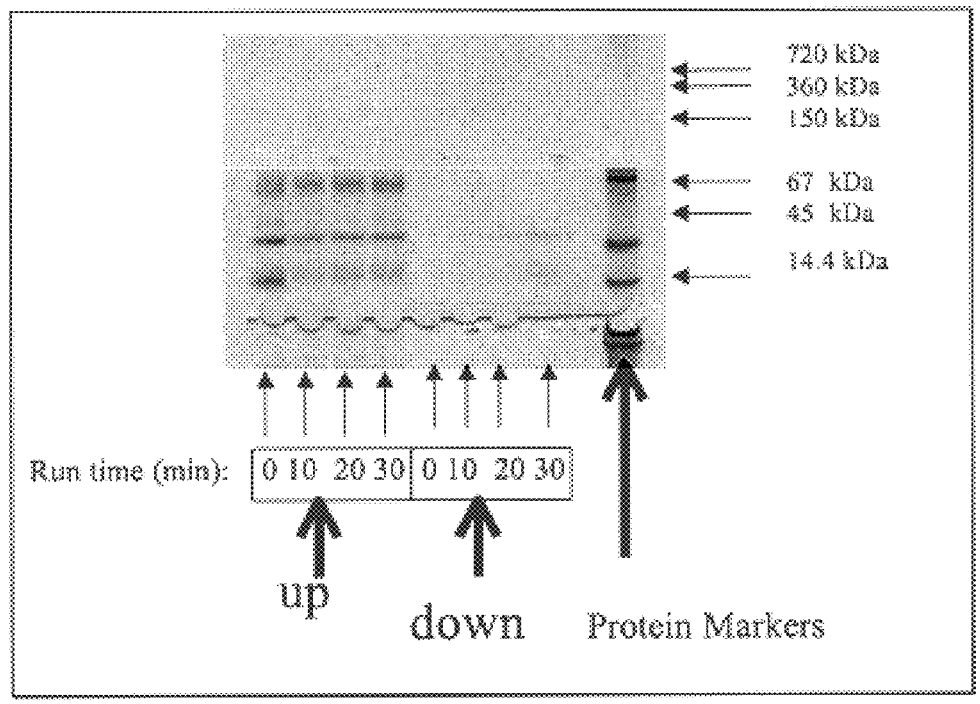
FIG. 16 shows the electrophoresis results from a 100 kDa membrane using photoinitiation and treated PET substrate as described in Example 14.

Membrane Performance: Treated PET substrate using 20/15 (%T, %C) (100 kDa) formulation A membrane with 100 kDa formulation using a surfactant treated PET sheet was produced. The Gradiflow™ test was performed and the electrophoresis results are shown in FIG. 16 (Electrophoresis results from 100 kDa membrane using photoinitiation and treated PET substrate). It is observed from this result that proteins with sizes less than 100 kDa went through from the up stream to the downstream.

EXAMPLE 15

47/16 (%T/%C) Membrane Formulation

A membrane with a 47/16 (%T/%C) formulation was produced according to Example 5 using PVA1 as the substrate. The membrane integrity was checked and the membrane used as a restriction membrane in a Gradiflow™ instrument.

EXAMPLE 16

8/4 (%T/%C) Membrane Formulation

A separation membrane was produced with an 8/4 (%T/%C) formulation according to the method described in Example 5 using PVA1 as a substrate. The membrane integrity was assessed and the membrane used to separate proteins using a Gradiflow™ instrument.

EXAMPLE 17

5/3 (%T/%C) Membrane Formation

A membrane with 1000 kDa (5/3%T/%C) formulation was produced (as per Example 5) using PVA1 paper as a substrate. And washed via an automated system. A leak test was performed to determine whether there were any defects in the membrane.

As can be seen foregoing disclosure of the present invention, in its preferred embodiments, the invention may provide supported membranes having the following features:

soluble entities eg monomer(s) to undetectable levels
High conversion
Mechanically strong, as thickness is not determined by the substrates thickness.
Less defects, due to the way of production.
Membranes with defined pore sizes Whilst the present invention has been described with particular reference to the production of acrylamide gels it will be clear that the membrane and method of the present invention can be used as separation media in not only electrophoresis but may also be used in membranes designed to separate biomolecules such as DNA. The membranes of the invention may also have application as a filtration membranes. Because of the thickness and strong mechanical strength of membranes in accordance with the invention, it is possible to provide a super-efficient filtration process.

It will be appreciated by those skilled in the art that numerous variations and/or modifications may be made to the present invention as shown in the specific embodiments without departing from the spirit and scope of the invention as broadly described. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

"Gradiflow" is a trademark of Gradipore Limited.

What is claimed is:

1. A polymeric membrane system comprising:
   a substrate containing a plurality of interstitial gaps, and
   a polymeric membrane comprised of polymeric membrane components residing within the interstitial gaps of the substrate and below the surface of the substrate, wherein the polymeric membrane components are thinner than the cross-sectional thickness of the substrate.

2. A polymeric membrane system according to claim 1 containing no detectable soluble entity.

3. A polymeric membrane system according to claim 2 containing no detectable water-soluble entities.

4. A polymeric membrane system according to claim 2 containing no detectable organic solvent soluble entities.

5. A polymeric membrane system according to claim 2 wherein the soluble entity is a monomer.

6. The polymeric membrane system according to claim 1 wherein the thickness of the polymeric membrane components is less than 0.5 mm.

7. The polymeric membrane system according to claim 1 wherein the thickness of the polymeric membrane components is less than 0.1 mm.

8. The poly membrane system according to claim 1 wherein the polymer membrane is an ultrathin membrane.

9. The polymeric membrane system according to claim 1 wherein the polymeric membrane is a hydrophilic polymer membrane.

10. The polymeric membrane system according to claim 1 wherein the polymeric membrane is a hydrophobic polymer membrane.

11. The polymeric membrane according to claim 1 wherein the polymeric membrane is formed from a crosslinked polymer.

12. The polymeric membrane system according to claim 11 wherein the polymeric membrane is a polyacrylamide gel.

13. The polymeric membrane system according to claim 11 wherein the polymeric membrane is a gel of PolyHEMA crosslinked with EDGMA.

14. The polymeric membrane system according to claim 12 wherein the polyacrylamide gel is formed from monomers having the formula $H_2C=CR^5$—CO—$NR^3R^4$ where $R^3, R^4$ and $R^5$ are each independently H or alkyl optionally monosubstituted by, for OH or $C(O)CH_2C(O)CH_3$.

15. The polymeric membrane system according to claim 12 or claim 14 wherein the polyacrylamide gel is formed from a crosslinking agent selected from N,N'-methylene bisacrylamide (BIS), ethylene glycol diacrylate, dihydroxy ethylene-bisacrylamide (DHEBA), N,N'-propylenebisacrylamide, diacrylamide dimethylether, 1,2-diacrylamide ethyleneglycol, ethyleneureabisacrylamide, N,N'-bisacrylylcystamine and bisacrylamide methylether (BAME).

16. The polymeric membrane system according to claim 14 wherein the polyacrylamide gel is produced by using Aam and the crosslinker monomer with the following formula:

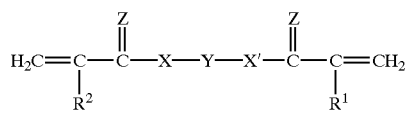

wherein

X and X' are independently selected from the group consisting of —O—, —S— and —NR—, where R is H, alkyl or cycloalkyl, $R^1$, $R^2$ is a $C_1$–$C_4$ alkyl group, Y is an optionally substituted non-aromatic divalent linking group, and Z is O or S.

17. The polymeric membrane system according to claim 14 wherein the crosslinker is a combination of crosslinkers at least one of which has at least three crosslinkable functional groups, wherein at least one of the crosslinkable functional groups is the group $CH_2=C(R)$—CO—, where R is H or optionally substituted alkyl.

18. The polymeric membrane system according to claim 17 wherein the crosslinker having at least three crosslinkable functional groups is a compount of Formula I or Formula II

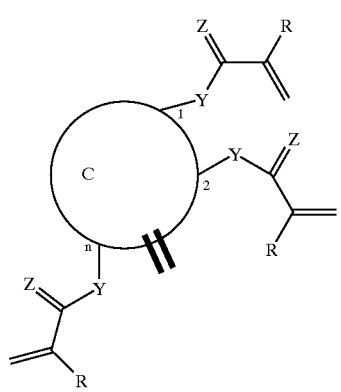

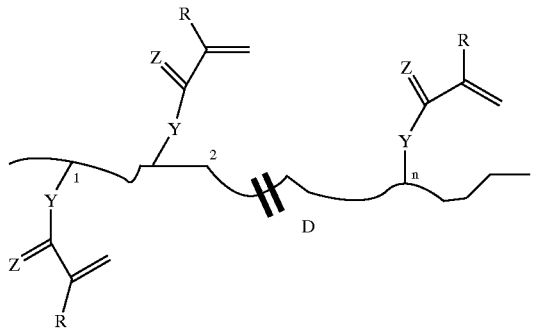

Wherein, in Formula I:

C represents a ring structure of the crosslinker molecule which is connected with at least 3 functional groups —Y—CZC(R)=$CH_2$ which functional groups may be the same or different;

Y in each functional group is independently selected from single bond, N, O or S;

Z in each functional group is independently selected from O or S; or Z may be two hydrogens, a hydrogen an optionally substituted alkyl, or two optionally substituted alkyl groups, and R in each functional group may be the same or different and selected from hydrogen or optionally substituted alkyl; and In Formula II:

D represents a backbone chain of the crosslinker which is connected with at least three functional groups —Y—CZC(R)—$CH_2$ which functional groups are the same or different;

Y in each functional group is the same or different and selected from the group consisting of a single bond, N, O or S;

Z in each functional group may is the same or different and selected from O or S; and R in each functional group is the same or different and selected from hydrogen or optionally substituted alkyl.

19. The polymeric membrane system according to claim 1, wherein the substrate is a woven or non-woven fabric or material.

20. The polymeric membrane system according to claim 1 wherein the substrate is formed from a material selected from the group consisting of polyvinyl alcohol, polyethyleneterapthalate, nylon and fiberglass.

21. The crosslinked polymeric membrane system according to claim 20 wherein the substrate is a polyvinyl alcohol sheet.

22. The crosslinked polymeric membrane system according to claim 20, wherein the substrate is formed from a non-woven polyethyleneterapthalate sheet, optionally treated with non-ionic surfactant. .

* * * * *